United States Patent [19]

Kumar

[11] Patent Number: 5,224,931
[45] Date of Patent: Jul. 6, 1993

[54] METHOD AND DEVICE FOR PERFORMING CHOLANGIOGRAPHY

[76] Inventor: Sarbjeet S. Kumar, 514 Brown St., Springfield, Tenn. 37172

[21] Appl. No.: 690,002

[22] Filed: Apr. 23, 1991

[51] Int. Cl.$^5$ ............................................... A61M 5/00
[52] U.S. Cl. .................................... 604/51; 604/174; 128/654; 606/205
[58] Field of Search ................... 606/205–209, 606/211; 128/4, 654, 656, 751, 752, DIG. 26; 604/51, 174, 272

[56] References Cited

U.S. PATENT DOCUMENTS

| | | | |
|---|---|---|---|
| 3,019,790 | 2/1962 | Militana | 606/205 |
| 3,814,080 | 6/1974 | Norman | 604/174 |
| 4,263,917 | 4/1981 | Moss | 128/656 |
| 4,484,911 | 11/1984 | Berlin et al. | 604/174 |
| 4,653,475 | 3/1987 | Seike et al. | 128/4 |
| 4,700,694 | 10/1987 | Shishido | 128/4 |
| 4,734,094 | 3/1988 | Jacob et al. | 128/656 |
| 4,735,617 | 4/1988 | Uddo, Jr. et al. | 128/DIG. 26 |
| 4,792,330 | 12/1988 | Lazarus et al. | 604/174 |
| 4,817,604 | 4/1989 | Smith, III | 604/174 |
| 5,071,412 | 12/1991 | Noda | 604/268 |

FOREIGN PATENT DOCUMENTS 316816  5/1989  European Pat. Off. ............ 606/205

OTHER PUBLICATIONS

Anderson, Grant's Atlas of Anatomy, 9th ed., ©1983 2-80 through 2-88.

*Primary Examiner*—Ralph Lewis
*Attorney, Agent, or Firm*—Mark J. Patterson; Edward D. Lanquist, Jr.; I. C. Waddey, Jr.

[57] ABSTRACT

The present device discloses a grasping forceps with side channel. A grasping forceps channel connects a clamp to a handle. The clamp is shut to close off the gall bladder to prevent gall stones from traveling from the gall bladder into the cystic duct and into the bile duct. The side channel is provided that is substantially parallel to the grasping forceps channel. The side channel directs a catheter into the ampulla on the side of the clamp proximate to the bile duct. This catheter has a needle for application of a dye to the ampulla.

14 Claims, 1 Drawing Sheet

– 5,224,931 –

METHOD AND DEVICE FOR PERFORMING CHOLANGIOGRAPHY

BACKGROUND OF THE INVENTION

The present invention relates generally to devices and techniques used in gall bladder surgery and more particularly to a method and device for performing a cholangiography at the time of gall bladder surgery, to assure that no stones from the gall bladder are retained in the bile ducts and related structures.

It will be appreciated by those skilled in the art that an important part of gall bladder surgery is cholangiography, which involves the injection of dye into the bile ducts at the time of surgery to assure that no stones from the gall bladder have passed into the bile ducts. After injection of a dye, an x-ray is taken. The developed x-ray outlines the bile ducts, thereby showing any stone or other abnormalities that need to be removed or corrected in the course of the surgical procedure.

Historically, when open surgery is performed, cholangiography is accomplished by inserting a plastic tube or catheter into the cystic duct which connects the gall bladder to the bile duct. This same method is currently being used in conjunction with laparoscopic cholecystectomy. Unfortunately, threading a catheter through a long hollow tube and into a cystic duct which is 3–4 mm in diameter is very difficult and technically frustrating, because of the size, bad angle, and catheter flexibility. The use of a rigid catheter will not work because it will not pass through the curved course. External support of the flexible catheter with a hollow metal tube has also failed to work satisfactorily.

Laparoscopic cholecystectomy was offered as an improvement to open surgery. Using this surgical technique, the gall bladder is removed by use of four 0.5 to 1.0 cm sized round metal tubes into the abdomen instead of an open surgical incision. A tube inserted through the navel carries a visualizing lens or laparoscope and camera that is connected to a video monitor, providing a picture of an internal view of the abdomen. Using long, narrow instruments inserted through three other small holes along the right upper part of the abdomen, the surgeon dissects and identifies the cystic duct which connects the gall bladder to the common bile duct. The surgeon also dissects and identifies the cystic artery. The cystic duct and artery are clipped and divided. The gall bladder is then removed, along with the contained stones. The surgical procedure appears to be quite successful, and patients can leave the hospital in a day instead of the four or five days required for recovery from open surgery. Patients can also return to work in as little as a week, instead of the four to six weeks of recovery required after open surgery.

A prior art method of performing a cholangiography is to clamp the gall bladder. A metal clip is then placed around the ampulla also known as the Hartman's Pouch or the infundibulum to prevent stones from flowing through the ampulla to the bile duct and to reduce leakage of bile from the gall bladder. Another metal tube is then placed into the abdomen. This metal tube directs a catheter into the cystic duct, between the ampulla and the common bile duct, after a small opening is cut into the cystic duct. Unfortunately, this method requires clamping, encircling, application of a different tube carrying the catheter, and placement of the dye into the cystic duct.

What is needed, then, is an improved method and device for performing a cholangiography. This needed method and device must allow the surgeon to prevent gall stones from exiting the gall bladder during cholecystectomy. This needed method and device must provide a rigid channel through which a needle can be directed, so that dye can be applied into the ampulla also known as the Hartman's Pouch or the infundibulum of the gall bladder. This method and device is presently lacking in the prior art.

SUMMARY OF THE INVENTION

In the present invention, a grasping forceps with a side channel is provided. The grasping forceps channel directs wire between the handle and clamp or forceps. A side channel directs a catheter with a needle in parallel with the grasping forceps channel. The grasping forceps with side channel are placed into the abdomen of the patient through a laparascopic cannula. The grasping forceps are closed proximate to and around the infundibulum also known as the Hartman's Pouch or the ampulla of the gall bladder to prevent stones from the gall bladder from traveling into the common bile duct and to prevent leakage of bile. The clamped forceps prevent the flow of bile into the gall bladder. The side channel then directs the catheter to penetrate the infundibulum also known as the Hartman's Pouch or the ampulla on the side of the infundibulum away from the gall bladder. Dye is then injected into the infundibulum. The clamped forceps prevent the dye from reaching the gall bladder.

Accordingly, an object of the present invention is to provide a device and method for performing a cholangiography.

Another object of the present invention is to provide a simple device for sealing off the ampulla to prevent stones from passing out of the gall bladder into the ampulla and into the common bile duct.

Another object of the present invention is to provide a simple device for sealing off the infundibulum to prevent dye from passing into the gall bladder.

Still another object of the present invention is to provide a unitary device for clamping the ampulla and directing a needle into the ampulla for injection of a dye.

DESCRIPTION OF THE PREFERRED EMBODIMENT

Figure 1:
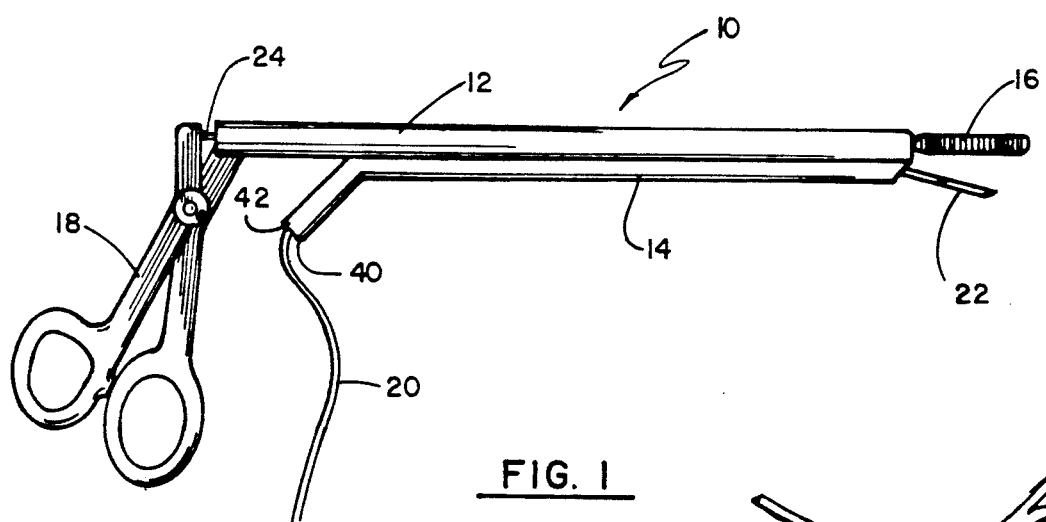
FIG. 1 is a side view of the grasping forceps with side channel of the present invention.

Referring now to FIG. 1, there is shown generally at 10 the grasping forceps with side channel of the present invention. Device 10 has grasping forceps channel 12 which directs wire 24 from handle 18 to clamp 16. As handle 18 is clamped together, clamp 16 closes. As handle 18 moves apart, clamp 16 opens. Device 10 is provided with side channel 14 which runs substantially parallel to channel 12. Through side channel 14 there is placed catheter 20. On end of side channel 14 proximate to clamp 16, needle 22 can be passed. The end of side channel 14 proximate to handle 18 is angled away from handle 18 to allow the user to feed catheter 20 without interference with handle 18.

Figure 2:
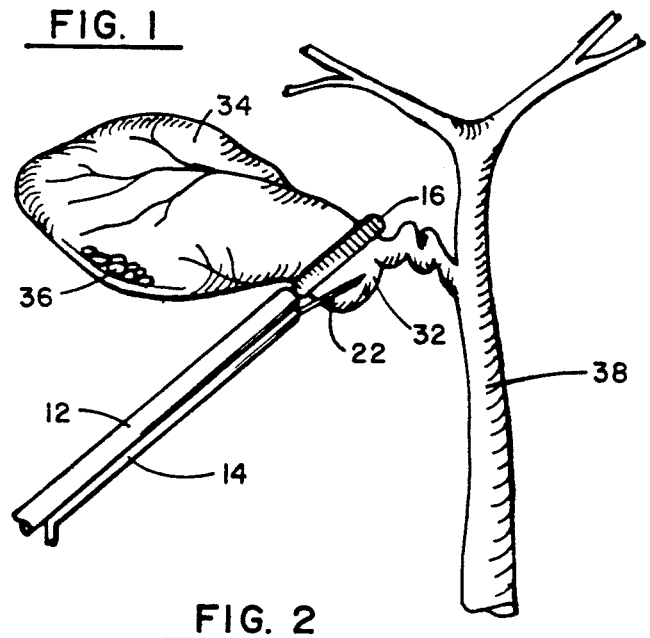
FIG. 2 is a cutaway view of the grasping forceps with side channel as it clamps the ampulla and penetrates the ampulla away from the gall bladder.
Figure 3:
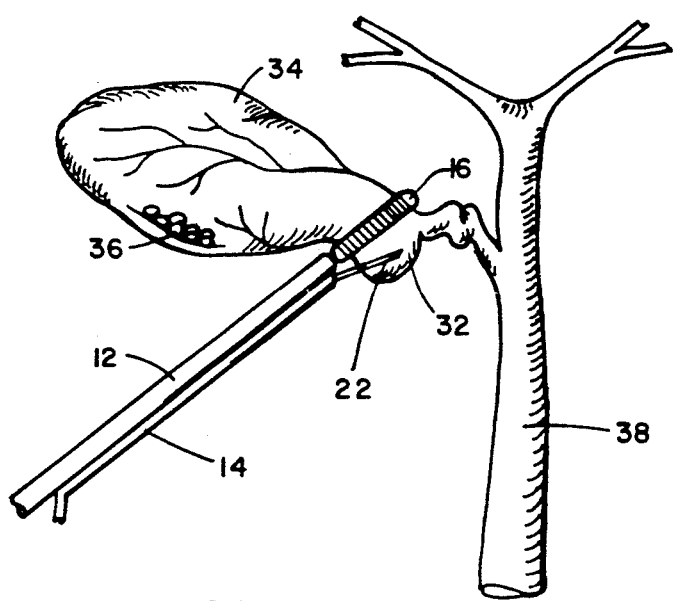
FIG. 3 is a cutaway view of the grasping forceps with side channel as it clamps the ampulla and applies dye into the ampulla through the extended catheter away from the gall bladder.

Referring now to FIG. 2, there is shown generally at 10 the device of the present invention. As one can see, clamp 16 closes around infundibulum 32 to prevent stones 36 in gall bladder 34 from passing into infundibulum 32 during a cholecystectomy. This clamp 16 prevents stones 36 in gall bladder 34 from also passing into common bile duct 38. After infundibulum 32 has been closed by clamp 16, needle 22 is directed through side channel 14. Needle 22 then administers dye into infundibulum 32 away from fundus 35 of gall bladder 34. Needle 22 punctures infundibulum 32 to apply dye. Back flow of dye into fundus 35 of gall bladder 34 is prevented by clamp 16. Therefore, dye can only travel into infundibulum 32 and on into bile duct 38. Ampulla 32 is also known as the Hartman's pouch or the infundibulum.

In the preferred embodiment, clamp 16 is substantially ¾ inch to 1 inch, to enable clamp 16 to clamp off entire infundibulum 32. In the preferred embodiment, the length of channel 14 is substantially 35 cm. However, any length may be used, as long as the surgeon is able to reach infundibulum 32. Needle 22 is, in the preferred embodiment, a 23 gauge needle and is substantially ¼ inch long.

In the preferred embodiment, device 10 enters stomach from the left side of the abdomen, angling to the right. Clamp 16 can have flat or serrated teeth. Clamp 16 can be curved.

In the preferred embodiment, device 10 is directed through a conventional surgical cannula. Channel 12 is substantially 3 mm in diameter, and side channel 14 is sized so that device 10 can pass through a standard 5 mm cannula.

In the preferred embodiment, end of side channel 14 proximate to handle 18 is angled away from handle 18 so as to allow the surgeon to feed catheter 20 through side channel 14 without interfering with handle 18. Further, to achieve a preferred angle of entry of needle 22 into the infundibulum, the distal or lower end of channel 14 should be cut at an angle such that an oval opening is created which will direct the needle 22 at approximately 15 to 20 degrees away from channel 12.

Prior to placement of device 10 into the cannula, carbon dioxide is placed into the abdomen through the cannula to enlarge the natural channels of the abdomen. After device 10 is placed in cannula, a certain amount of pressure of $CO_2$ is applied to the cannula to ensure that the proper amount of carbon dioxide remains in the abdomen. To ease application of the dye through catheter 20, end of side channel 14 proximate to handle 18 is angled away from channel 12. Stopper 40 is placed in opening 42 of end of side channel 14 proximate to handle 18 to ensure that liquid and gas do escape through channel 14. Stopper 40 could conceivably be placed in other end of channel 14. However, this may interfere with catheter 20.

Thus, although there have been particular embodiments of the present invention of a new and useful method and device of cholangiography, it is not intended that such references be construed as limitations upon the scope of this invention, except as set forth in the following claims. Further, although there have been described certain dimensions used in the preferred embodiment, it is not intended that such dimensions be construed as limitations upon the scope of this invention, except as set forth in the following claims.

What I claim is:

1. A method of injecting dye into the infundibulum of the gallbladder for cholangiography in conjunction with surgical removal of a gallbladder comprising the steps of:
   (a) clamping said infundibulum of said gallbladder with a grasping means attached to means to direct a dye application means;
   (b) directing said dye application means through said means to direct a dye application means until said dye application means penetrates said infundibulum on the side of said grasping means distally located from said fundus; and
   (c) applying dye through said dye application means.

2. The method of claim 1 wherein said grasping means comprises an elongated grasping jaws attached to means to direct a dye application means.

3. The method of claim 1 wherein said directing means comprises a side-channel connected to said grasping means.

4. The method of claim 3 wherein:
   a. said grasping means comprises an elongated grasping jaws attached to said means to direct a dye application means; and
   b. said side-channel is in substantial parallel alignment with said elongated grasping jaws.

5. A grasping forceps for performing cholangiography through the infundibulum of a gallbladder comprising:
   (a) an elongated member having a proximal end and a distal end;
   (b) a means for clamping said infundibulum fixed to said distal end of said elongated member;
   (c) a side-channel extending from said proximal end to said distal end of said elongated member having an opening adjacent to said means for clamping said infundibulum;
   (d) means slidably received by said side-channel for applying a dye into said infundibulum attached to said means for clamping said infundibulum.

6. The device of claim 5 wherein said gallbladder clamp means comprises an elongated clamp jaws substantially at least 1 inch long.

7. The device of claim 6 wherein said means for applying a dye into said infundibulum comprises:
   (a) a catheter means having a distal end; and
   (b) an infundibulum penetration means received by said catheter means, said infundibulum penetration means attached to and in fluid communication with said catheter means distal end.

8. The device of claim 7 wherein said infundibulum penetration means comprises a needle attached to said catheter means in fluid communication.

9. A device for application of a dye during a cholangiography comprising:
   (a) a handle means;
   (b) an elongated member having a proximal end and a distal end, said handle means connected to said proximal end;
   (c) clamp means fixed to said distal end of said elongated member for clamping said infundibulum of said gall bladder;
   (d) an elongated channel means extending through said elongated member means from said proximal end to said distal end; and (e) means for applying dye slidably received within said channel means.

10. The device of claim 9 wherein said clamp means comprises elongated jaws.

11. The device of claim 9 wherein said means to apply dye into an infundibulum comprises:

(a) a catheter means having a distal end; and (b) an ampulla penetration means attached to and in fluid communication with said catheter means distal end.

12. The device of claim 11 wherein said ampulla penetration means comprises an injecting needle attached to said catheter means.

13. The device of claim 12 wherein a central axis of said injecting needle is directed approximately 15 to 20 degrees away from a central axis of said channel means.

14. The device of claim 9 wherein said clamp means comprises grasping jaws.

* * * * *